(12) United States Patent
Dobler et al.

(10) Patent No.: US 7,141,698 B2
(45) Date of Patent: Nov. 28, 2006

(54) CONTINUOUS PROCESS FOR PRODUCING PSEUDOIONONES AND IONONES

(75) Inventors: Walter Dobler, Schwetzingen (DE); Nicolaus Bahr, Heidelberg (DE); Klaus Breuer, Altrip (DE); Alois Kindler, Grünstadt (DE)

(73) Assignee: BASF Aktiengesellschaft (DE)

( * ) Notice: Subject to any disclaimer, the term of this patent is extended or adjusted under 35 U.S.C. 154(b) by 0 days.

(21) Appl. No.: 10/533,969

(22) PCT Filed: Oct. 28, 2003

(86) PCT No.: PCT/EP03/11926

§ 371 (c)(1),
(2), (4) Date: May 5, 2005

(87) PCT Pub. No.: WO2004/041764

PCT Pub. Date: May 21, 2004

(65) Prior Publication Data

US 2006/0014984 A1   Jan. 19, 2006

(30) Foreign Application Priority Data

Nov. 7, 2002  (DE) ............................. 102 52 259

(51) Int. Cl.
*C07C 45/72* (2006.01)
(52) U.S. Cl. .................. 568/343; 568/376; 568/390
(58) Field of Classification Search .................. None
See application file for complete search history.

(56) References Cited

U.S. PATENT DOCUMENTS

| | | | |
|---|---|---|---|
| 3,480,677 A | | 11/1969 | Meuly et al. |
| 3,840,601 A | * | 10/1974 | Gradeff .................... 568/390 |
| 4,431,844 A | | 2/1984 | Janitschke et al. |
| 4,874,900 A | | 10/1989 | Mitchell |
| 5,914,012 A | | 6/1999 | Kaibel et al. |
| 6,140,542 A | | 10/2000 | Rheude et al. |
| 6,288,282 B1 | | 9/2001 | Rheude et al. |

FOREIGN PATENT DOCUMENTS

| | | |
|---|---|---|
| DE | 31 14 071 | 10/1982 |
| DE | 33 02 525 | 7/1984 |
| DE | 33 19 430 | 11/1984 |
| DE | 196 19 557 | 11/1997 |
| EP | 0 062 291 | 10/1982 |
| EP | 0 295 361 | 12/1988 |
| EP | 0 804 951 | 11/1997 |
| PL | 147 748 | 6/1988 |
| SU | 704 938 | 12/1979 |
| WO | WO-97/43254 | 11/1997 |

\* cited by examiner

OTHER PUBLICATIONS

Database WPI, Section Ch, Week 198032, Derwent Publications Ltd., XP002267975.

*Primary Examiner*—Sikarl A. Witherspoon
(74) *Attorney, Agent, or Firm*—Connolly Bove Lodge & Hutz

(57) ABSTRACT

The invention relates to a continuous process for producing pseudoionones of general formulas (I) and (I') as well as isomers thereof, whereby: $R^1$ represents $CH_3$ or (a); $R^2$ and $R^3$ represent hydrogen, $CH_3$ or $C_2H_5$, and; $R^4$ and $R^5$ represent hydrogen or $CH_3$. These pseudoionones are produced by reacting an aldehyde of formula (II) with an excess of a ketone of general formula (III), whereby $R^1$, $R^2$ and $R^3$ have the aforementioned meanings, in the presence of water and alkali hydroxide at an increased temperature and in a homogeneous solution. The inventive process is characterized in that: a) the intermixing of the homogeneous solution consisting of aldehyde, ketone and aqueous alkali lye occurs at a temperature ranging from 10 to 120° C.; b) the undissolved water and alkali hydroxide contained in the reaction mixture are subsequently separated out; c) while avoiding back mixing, the homogeneous reaction mixture is then guided through a reactor, which permits a residence time ranging from 2 to 300 minutes, at a temperature that is 10 to 120° C. higher than the boiling point of the lowest-boiling component and under a vapor pressure p ranging from $10^6$ to $10^7$ Pa; d) the reaction mixture is cooled by expansion; e) ketone is removed from the reaction mixture using vapor flowing in the opposite direction and; f) the raw product is dried and rid from excessive aldehyde and secondary components via a rectification column

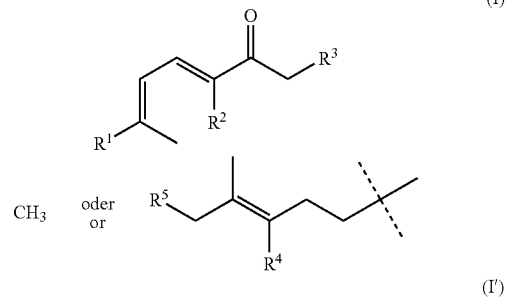

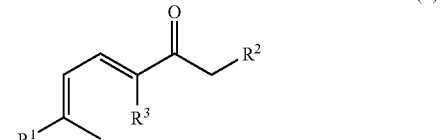

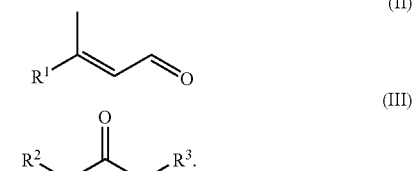

18 Claims, No Drawings

CONTINUOUS PROCESS FOR PRODUCING PSEUDOIONONES AND IONONES

RELATED APPLICATIONS

This application is a national stage application (under 35 U.S.C. 371) of PCT/EP2003/011926 filed Oct. 28, 2003 which claims benefit to German application 102 52 259.6 filed Nov. 7, 2002.

The present invention relates to a continuous process for preparing pseudoionones and the optional subsequent cyclization thereof to ionones. Preference is given to the process for preparing compounds such as 6-methylhepta-3,5-dien-2-one, pseudoionone, methylpseudoionone, dimethylpseudoionone, pseudoirone, methylpseudoirone and dimethylpseudoirone and the cyclization products thereof, α-, β- and γ-ionone, α-, β- and γ-methylionone (n-form, iso-form or mixtures), and homologs. These substances are of great economic significance as odorants and odorant intermediates. Pseudoionone itself is additionally a significant intermediate for the preparation of vitamins E and A and of carotinoids. β-Ionone is a significant intermediate for the preparation of vitamin A and carotinoids.

For the preparation of pseudoionones from citral, numerous methods are known.

PL 147748 describes a process for preparing ionones by condensing citral and acetone over basic ion exchangers at 56° C. According to this, acetone and citral are stirred with the catalyst in a flask batchwise for 5 hours. A disadvantage of this process is the very low space-time yields.

DE-A 33 19430 teaches the preparation of higher ketones by condensing methyl ketones and unsaturated aldehydes over mixed metal catalysts in the presence of hydrogen at from 100 to 280° C. and from 10 to 60 bar in a tubular reactor.

A process for preparing pseudoionones by reacting citral with acetone using LiOH as a catalyst is described in U.S. Pat. No. 4,874,900. According to this, the reaction is carried out batchwise or continuously at temperatures of from −20 to 240° C. The pressure is adjusted such that the reaction mixture remains in the liquid phase at the appropriate temperature. In the case of batchwise operation, the reactants are stirred in a tank and the catalyst is filtered off on completion of the reaction, while, in the continuous mode, the premixed reactants are pumped through a column filled with catalyst. In both cases, the reaction mixture is neutralized with $CO_2$ after the end of the reaction and the excess ketone is distilled off. In this process, at a molar acetone to citral ratio of 20, yields of 89.5% citral are obtained. These low yields are unsatisfactory for an industrial scale process.

DE-A 31 14071 describes a process for preparing pseudoionones by reacting an aldehyde with an excess of a ketone at elevated temperature.

The prior art also discloses numerous methods for the subsequent cyclization of pseudoionones to ionones. For instance, it is known that mixtures of α- and β-ionones are obtained in the cyclization of pseudoionones with acids such as concentrated sulfuric acid or phosphoric acid. The ratio of the amounts in which these compounds are formed depends greatly upon the conditions under which the reaction takes place.

In cyclizations with concentrated sulfuric acid, which proceed highly exothermically, it is important to remove the heat of reaction very rapidly in order to prevent localized hotspots. For this purpose, diluents are added to the reaction mixture in the known processes.

It is an object of the present invention to develop a process for preparing pseudoionones and for cyclization to the corresponding ionones which follows if appropriate, which needs fewer feedstocks in comparison to the prior art and generates more product per feedstock.

1. According to the invention, the object is achieved by providing a continuous process for preparing pseudoionones of the general formulae I or I' and isomers thereof

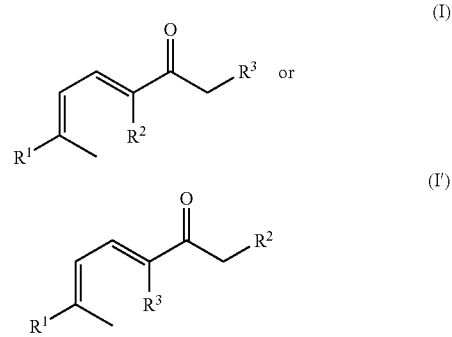

where $R^1$ is

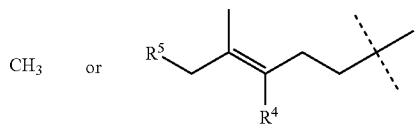

$R^2$, $R^3$ are each hydrogen, $CH_3$ or $C_2H_5$,
$R^4$, $R^5$ are each hydrogen or $CH_3$,
by reacting an aldehyde of the formula (II)

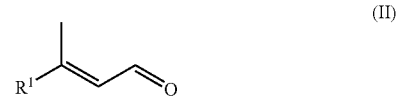

with an excess of a ketone of the general formula (III)

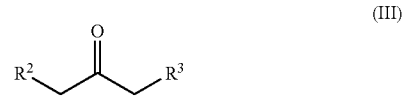

where $R^1$, $R^2$ and $R^3$ are each as defined above, in the presence of water and alkali metal hydroxide at elevated temperature in homogeneous solution, which comprises a) mixing the homogeneous solution of aldehyde, ketone and aqueous alkali metal hydroxide at a temperature of from 10 to 120° C., then b) removing the water and alkali metal hydroxide which have not dissolved in the reaction mixture, c) subsequently passing the homogeneous reaction mixture, avoiding backmixing, at a temperature which is from 10 to 120° C. above the boiling point of the lowest-boiling component and a vapor pressure p of from $10^6$ to $10^7$ Pa through a reactor which enables a residence time of from 2 to 300 minutes, d) cooling the reaction mixture under decompression, e) removing the ketone from the reaction mixture with steam in countercurrent and f) drying the crude product and freeing it of excess aldehyde and secondary components using a rectification column.

Preference is given to using the process according to the invention for preparing 6-methylhepta-3,5-dien-2-one, pseudoionone, methylpseudoionone, dimethylpseudoionone, pseudoirone, methylpseudoirone and dimethylpseudoirone and isomers thereof.

The aldehydes used in accordance with the invention are preferably citral, citronellal and 2,6-dimethyloctanal, but also any straight-chain or branched, saturated or else unsaturated, aldehyde having from 1 to 10 carbon atoms, and the ketones used are preferably acetone, 2-butanone, or 2- or 3-pentanone.

Aqueous alkali metal hydroxide refers to an aqueous solution of potassium hydroxide, sodium hydroxide or lithium hydroxide, but preferably sodium hydroxide solution. The concentration of the alkali metal hydroxide used is between 0.005 and 50% by weight, preferably between 1 and 15% by weight.

The isomers refer to all possible positional isomers or double bond isomers of the pseudoionones or ionones.

In the process according to the invention, only as much alkali metal hydroxide solution is added at from 10 to 120° C., preferably at temperatures of less than 50° C., to the homogeneous mixture of the aldehyde, ketone and water reactants as dissolves homogeneously after intimate mixing. Any water and alkali metal hydroxide which separates is removed, before the homogeneous reaction mixture is passed, while avoiding backmixing, at a temperature which is from 10 to 120° C. above the boiling point of the lowest-boiling component and a pressure p of from $10^6$ to $10^7$ Pa where p is the vapor pressure of the reaction mixture at the reaction temperature, through a reactor which enables a residence time of from 2 to 300 minutes, preferably from 5 to 30 minutes. The reaction mixture is cooled by decompression, in the course of which a portion of the ketone excess evaporates and can be fed to recycling, then the ketone is removed from the reaction mixture with steam in countercurrent, the steam containing enough of an evaporable acid that the catalyst base is neutralized, and a pH of from 4 to 9 is established. Subsequently, the crude product is dried and freed of excess aldehyde and secondary components using a rectification column, preferably using a dividing wall column, as disclosed, for example, in DE-A 3302525 or in EP-A 804 951.

The invention further provides a continuous process for preparing ionones of the general formulae (IV), (V) and (VI) and isomers thereof, which comprises converting the pseudoionones obtained by the process according to the invention to ionones of the general formulae (IV)–(VI)

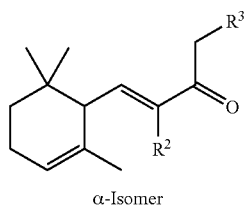

α-Isomer
(IV)

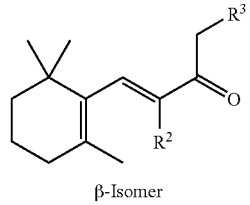

β-Isomer
(V)

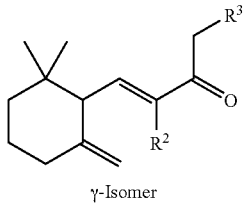

γ-Isomer
(VI)

It is surprising that the formation of secondary and decomposition products which arises as a side reaction in the heterogeneous catalysis by alkali metal hydroxide, in particular the workup of the reaction mixture, can be suppressed when the mixture of ketone and aldehyde is admixed below the process temperature in the reactor only with as much alkali metal hydroxide solution as can be dissolved homogeneously, and the homogeneous mixture saturated with aqueous alkali metal hydroxide solution is brought to the desired reaction temperature under autogenous pressure in a tubular reactor without further mixing.

It is advantageous to remove at the reactor inlet any alkali metal hydroxide solution occurring which has not dissolved into the mixture and is thus excess. This may be effected in a separator which is either attached upstream of the reactor or is integrated into the bottom of the reactor. It is also advantageously possible to remove excess water from the ketone to be recycled by metering into the reaction mixture highly concentrated, i.e. from about 10 to 50%, preferably from 35 to 45%, alkali metal hydroxide solution, which dehydrates the reaction mixture and dissolves the required amount of alkali metal hydroxide into the reaction mixture.

The reaction is conducted with a from 5–50-fold, preferably with a from 20–25-fold, molar excess of ketone in order to achieve an optimal yield based on the aldehyde used. The unconverted ketone fraction is removed downstream of the reaction zone at a pressure of from $10^7$ to $10^9$ mPa$_{abs}$ and fed back to the fresh ketone for the synthesis.

Surprisingly, the water content of the aldehyde-ketone mixture is also of particular significance. This apparently determines the amount of alkali metal hydroxide which can be dissolved homogeneously in the aldehyde-ketone mixture. The water content of the aldehyde-ketone mixture should be between 1 and 15% by weight. The amount of alkali metal hydroxide dissolved in turn determines the conversion rate, but also influences the occurrence of undesired by-products. This is in agreement with the fact that the removal of excess alkali upstream of the reactor is advantageous. In contrast to the prior art, this prevents further dissolution of alkali metal hydroxide into the reaction mixture toward the end of the reaction owing to the increase in the water content due to the water of reaction, which promotes by-product formation in this phase. The latter plays a significant role in particular in the case of sensitive unsaturated aldehydes, for example citral, and reduces the yield.

The water is advantageously introduced into the process via the proportion which is within the ketone component and is generated downstream of the reactor by the steam stripping of the reaction mixture. It is of economic significance that this allows the ketone excess to be removed with low technical complexity and energy intensity, since the complicated drying before the recycling becomes superfluous. Alternatively, it is also possible to proceed with an anhydrous mixture of aldehyde and ketone and mix in the water required (from about 1 to 15% by weight), by using a very dilute alkali metal hydroxide solution. Conversely, it is possible to use a mixture of aldehyde and ketone having a very high content of water when a concentrated alkali metal hydroxide solution is mixed in. In this case, a lower mixing temperature is required in order to prevent the uncontrolled start of the reaction. At the same time, the consumption of alkali metal hydroxide rises, since it is only partly transferred into the organic phase. It partly dehydrates the aldehyde-ketone mixture and has to be removed and disposed of.

The homogeneous reaction solution is heated in a tubular reactor under autogenous pressure, and the reaction temperature at a given residence time is adjusted such that the conversion of the aldehyde component is from 60 to 98%, preferably from 85 to 95%, and the unconverted aldehyde is removed and recycled into the reaction. The tubular reactor is dimensioned such that the average residence time is between 2 and 300 minutes, preferably between 5 and 30 minutes, in such a way that there is very little backmixing. Higher conversions entail disproportionately raising the reaction temperature, which promotes by-product formation. Lower conversions enable a lower reaction temperature, which suppresses the by-product occurrence, but the ketone and aldehyde recycle streams, and thus the energy demands of the process, increase.

In the tubular reactor, the backmixing has to be minimized. This can be achieved by a sufficiently large reactor diameter in order to avoid turbulence, or else also by laminar-flow internals of any type. This is surprising and is in contradiction to the prior art, where, for example, according to DE-A 31 14 071, tubular reactors have to have such a design that there is a sufficiently turbulent flow under the reaction conditions.

The reaction mixture is decompressed to standard pressure, in the course of which it cools via the evaporation of a portion of the excess ketone. The remaining ketone is driven out in a countercurrent column with steam to which has been added an equimolar amount of a volatile acid, in the course of which the catalyst base is neutralized and diluted by the condensate. The use of column packings ensures that no significant amounts of further products in addition to ketone and water are obtained at the top of the column, and the reflux to the column is advantageously adjusted in such a way that the ketone can be drawn off with the desired amount of water. The amount of acid is advantageously such that the pH of from 4 to 9 favorable for the further workup is established at this point. After removal of the aqueous phase, the crude product is dried, by heating it and spraying it into a flash vessel which is kept under reduced pressure. From there, the mixture is transferred into a rectification column in which the unsaturated ketone is purified under reduced pressure to free it of impurities and the unconverted aldehyde is removed and fed from there to the recycling. The recycling is effected advantageously in a dividing wall column as described in EP-A 804 951, which preferably has 2 side draws in order to obtain both main fractions (product and aldehyde) in sufficient purity in one step.

The above-described process has very particular significance when citral is used as the aldehyde component and 2-butanone as the ketone component. A characteristic mixture of 70–97% n-methylpseudoionone and 3–30% isomethylpseudoionone is formed and can be cyclized to give a characteristic mixture of methylionones. Methylionones exist in highly varying isomer ratios. Each of them is used by the odorants industry in a large amount for producing industrial perfumes. Since each isomer ratio has a somewhat different fragrance note, the reproducibility of an isomer ratio once used is of utmost importance.

To prepare the corresponding ionones, the resulting mixture of pseudoionones is reacted with highly concentrated, i.e. from about 50 to about 98%, sulfuric acid, in the presence of a diluent which is inert under the reaction conditions, more advantageously as described in DE 196 19 557. In a departure therefrom, cyclization temperatures of <20° C. and a sulfuric acid concentration of <90% are advantageous when a residence time of >10 seconds is maintained between cyclization and hydrolysis. In the case of methylionones, a sulfuric acid concentration of about 89% at a residence of about 2 min at about 25° C. is advantageous, in which case almost exclusively the β-isomers are obtained, while the formation of α-n- and γ-n-methylionones is suppressed to about 1%. In the case of pseudoionone, virtually exclusively β-ionone is formed in high yield with 89% sulfuric acid, while α-ionone and γ-ionone are only within the 1% range and can be removed overhead in the purifying distillation without any problem.

The examples which follow will illustrate the invention in detail, but without restricting it thereto.

EXAMPLE 1

Preparation of Pseudoionone 370 kg/h of citral (2.43 kmol/h), approx. 26 kg/h of recycled citral, 3800 kg/h of aqueous 95% acetone and 30 kg/h of 5% aqueous NaOH are mixed. This forms a homogeneous solution which is passed through a phase separator as a precaution. When the water content or else the NaOH content is higher than specified, an aqueous phase can separate after the mixing process and has to be separated out. The mixture is heated to 108° C. and pumped through a 160 l tubular reactor. The heat of reaction heats the mixture further to approx. 112° C. At a residence time of approx. 2 min, a conversion of approx. 93% is achieved.

The reaction mixture from the tubular reactor is decompressed to standard pressure. In the course of this, approx. 2000 l/h of acetone distill off, and the product solution cools to approx. 60° C. Subsequently, the mixture is freed of residual acetone in countercurrent with approx. 700 kg/h of steam. Sufficient acetic acid is added to the steam that the sodium hydroxide solution in the mixture is neutralized and the effluent, aqueous mixture has a pH of 4–5. The acetone is recycled back into the process.

Removal of the aqueous phase is followed by drying at approx. 100° C. and approx. 50 mbar and distillative purification in a dividing wall column having 2 side draws. At the lower side draw, approx. 400 kg/h of pseudoionone having a purity of 98% are obtained (GLC area %, sum of all isomers!). At the upper side draw, approx. 26 kg/h of citral are obtained (sum of all isomers) and are recycled continuously into the process.

EXAMPLE 2

Methylpseudoionones 110 kg/h of citral (0.72 kmol/h), approx. 20 kg/h of recycled citral (0.13 kmol/h), 1800 kg/h of aqueous 82% 2-butanone and approx. 20 kg/h of 5% aqueous NaOH are mixed. This forms a homogeneous solution which is passed through a phase separator as a precaution. When the water content or else the NaOH content is higher than specified, an aqueous phase can separate after the mixing process and has to be separated out. The mixture is heated to 136° C. and pumped through a 160 l tubular reactor. The heat of reaction heats the mixture further to approx. 138° C. Within a residence time of 4 minutes, a conversion of approx. 82% based on citral is attained.

Removal of the aqueous phase is followed by drying at approx. 100° C. and approx. 50 mbar and distillative purification in a dividing wall column having 2 side draws. At the lower side draw, approx. 100 kg/h of methylpseudoionone having a purity of 98% are obtained (GLC area %, sum of all isomers!). At the upper side draw, approx. 20 kg/h of citral are obtained (sum of all isomers) and are recycled continuously into the process.

An iosmer ratio of about n: iso=5:1 is attained.

EXAMPLE 3

Methylpseudojonones 100 kg/h of citral (0.66 kmol/h), approx. 25 kg/h of recycled citral (0.16 kmol/h), 2200 l/h of aqueous 88% 2-butanone and approx. 120 kg/h of 40% aqueous NaOH are mixed. This forms a biphasic solution which is passed through a phase separator. Approx. 120 kg/h of aqueous NaOH are removed and approx. 2100 kg/h of organic phase are heated at 120° C. and pumped through a 160 l tubular reactor. The heat of reaction heats the mixture further to approx. 132° C. At a residence time of 4 minutes, a conversion of approx. 75% based on citral is attained.

The reaction mixture from the tubular reactor is decompressed to standard pressure. In the course of this, 1000 l/h of 2-butanone distill off, and the product solution cools to approx. 75° C. Subsequently, the mixture is freed of residual 2-butanone in countercurrent with approx. 550 kg/h of steam. Sufficient acetic acid is added to the steam that the sodium hydroxide solution in the mixture is neutralized and the effluent, aqueous mixture has a pH of 4–5.

Excess 2-butanone is recycled back into the process.

Removal of the aqueous phase is followed by drying at approx. 100° C. and approx. 50 mbar and distillative purification in a dividing wall column having 2 side draws. At the lower side draw, approx. 100 kg/h of methylpseudoionones having a purity of 98% are obtained (GLC area %, sum of all isomers). At the upper side draw, approx. 25 kg/h of citral are obtained (sum of all isomers) which are recycled continuously into the process.

An isomer ratio of about n:iso=8:1 is obtained.

EXAMPLE 4

Methylionones

Approx. 140 l/h of methylpseudoionones, 400 l/h of hexane (precooled to −8° C.!) and 200 l/h of 89% sulfuric acid are intimately mixed successively in a reaction pump. The reaction mixture heats spontaneously to approx. 29° C., and is cooled to about 26° C. and circulated by pumping in a delay zone at this temperature for approx. 2 min, before it is diluted with approx. 600 l/h of water in a further reaction pump. The mixture heats as a result of the addition of water to approx. 47° C. and is kept at <45° C. using a downstream cooler. After the water phase having a high sulfuric acid content is removed and, after further water scrubbing, the hexane is removed in countercurrent with steam. The hexane is recycled back into the reaction.

Removal of the aqueous phase is followed by drying at approx. 50 mbar and 100° C. and purification in a dividing wall column having 2 side draws. In the main fraction (side draw 1), approx. 120 l/h of methylionones having a content of β-n-methylpseudoionone between 80 and 90% are obtained.

The table which follows lists one of the typical compositions[1]:

| | | | |
|---|---|---|---|
| α-isomethylionone | 8.8% ± 1 | Sum of isomethylionones | 10.7% ± 1.6 |
| β-isomethylionone | 0.8% ± 0.1 | | |
| γ-isomethylionone | 1.1% ± 0.5 | | |
| α-n-methylionone | 0.25% ± 0.1 | Sum of n-methylionones | 85.5% ± 1.8 |
| β-n-methylionone | 85.0% ± 1.5 | | |
| γ-n-methylionone | 0.3% ± 0.2 | | |

[1] E- and Z-isomers are detected together, and the E-isomers dominate.

What is claimed is:

1. A continuous process for preparing pseudoionones of the general formulae I or I' and isomers thereof where $R^1$ is $CH_3$ or $R^2$, $R^3$ are each hydrogen, $CH_3$ or $C_2H_5$,
$R^4$, $R^5$ are each hydrogen or $CH_3$,
by reacting an aldehyde of the formula (II)

with an excess of a ketone of the general formula (III)

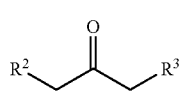 (III)

where $R^1$, $R^2$ and $R^3$ are each as defined above, in the presence of water and alkali metal hydroxide at elevated temperature in homogeneous solution, which comprises mixing the homogeneous solution of aldehyde, ketone and aqueous alkali metal hydroxide at a temperature of from 10 to 120° C., then removing the water and alkali metal hydroxide which have not dissolved in the reaction mixture, subsequently passing the homogeneous reaction mixture, avoiding backmixing, at a temperature which is from 10 to 120° C. above the boiling point of the lowest-boiling component and a vapor pressure p of from $10^6$ to $10^7$ Pa through a reactor which enables a residence time of from 2 to 300 minutes, cooling the reaction mixture under decompression, removing the ketone from the reaction mixture with steam in countercurrent and drying the crude product and freeing it of excess aldehyde and secondary components using a rectification column.

2. The process according to claim 1, wherein the ketone component of the general formula (II) is added in a from 5- to 50-fold molar excess, and the unconverted proportion, downstream of the reaction zone, is removed at a pressure of from $10^7$ to $5-10^8$ $mPa_{abs}$ and added again to the fresh ketone for the synthesis.

3. The process according to claim 1, wherein the reaction temperature at a given residence time is selected in such a way that the conversion of the aldehyde component is from 60 to 98%, and the unconverted aldehyde is removed and recycled into the reaction.

4. The process according to claim 1, wherein the water content of the ketone, used for the reaction, of the formula (III) is between 1 and 15% by weight.

5. The process according to claim 1, wherein the concentration of the alkali metal hydroxide used for the reaction is between 0.005 and 50% by weight.

6. The process according to claim 1 for preparing pseudoionones of the formula I and isomers thereof where $R^2$ or $R^3$ is methyl, wherein the concentration of the alkali metal hydroxide used for the reaction is from 10 to 50% by weight.

7. The process according to claim 1, wherein the ketone of the formula (III) used consists substantially of excess ketone of the formula (III) which has been removed from the reaction and has a water content of 1–15% by weight, which may be supplemented with either anhydrous or aqueous ketone of the formula (III) having a water content of 1–15% by weight.

8. The process according to claim 1, wherein, in the case of reaction with ketones of the general formula (III) where $R^2 \neq H$ and $R^3 = H$, a product mixture is obtained which contains from 70 to 95% n-alkylpseudoionones and from 5 to 30% isoalkylpseudoionones

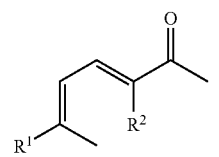
iso-alkylpseudoionone

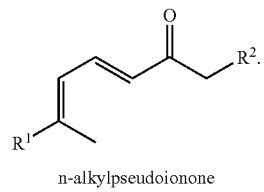
n-alkylpseudoionone

9. A continuous process for preparing ionones of the general formulae (IV), (V) and (VI) and isomers thereof, which comprises reacting the pseudoionones obtained according to claim 1 to give ionones of the general formulae (IV) to (VI)

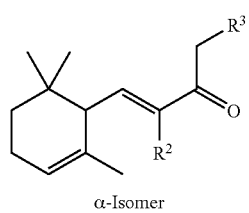
α-Isomer (IV)

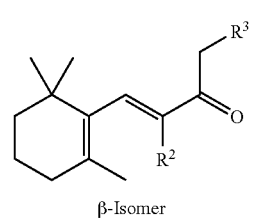
β-Isomer (V)

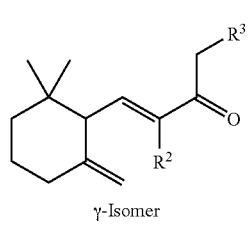
γ-Isomer (VI)

in the form such that the ratio of the n-form ($R^2$=H, $R^3$=alkyl) to the iso-form ($R^2$=alkyl, $R^3$=H) is maintained.

10. The process according to claim 9, wherein the pseudoionones are reacted with highly concentrated sulfuric add in the presence of a dihient which is inert under the reaction conditions to give ionones, the reaction temperature being 0–20° C. and the residence time between cyolization and hydrolysis being from 10 to 300 seconds.

11. The process according to claim 3, wherein the water content of the ketone, used for the reaction, of the formula (III) is between 1 and 15% by weight.

12. The process according to claim 11, wherein the concentration of the alkali metal hydroxide used forte reaction is between 5 and 10% by weight.

13. The process according to claim 12 for preparing pseudoiones of the formula I and isomers thereof where $R^2$ or $R^3$ is methyl, wherein the concentration of the alkali metal hydroxide used for the reaction is from 35 to 45% by weight.

14. The process according to claim 13, wherein the ketone of the formula (III) used consists substantially of excess ketone of the formula (III) which has been removed from the reaction and has a water content of 1–15% by weight, which may be supplemented with either anhydrous or aqueous ketone of the formula (III) having a water content of 1–15% by weight.

15. The process according to claim 14, wherein, in the case of reset on with ketones of the general formula (III) where $R^2 \neq H$ and $R^3 = H$, a product mixture is obtained which contains from 70 to 95% n-alkylpseudoionones and from 5 to 30% isoalkylpseudoionones

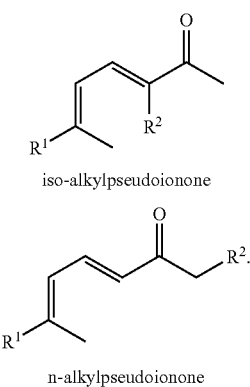

iso-alkylpseudoionone

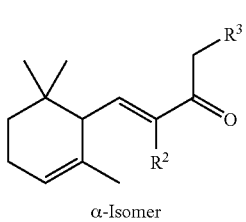

n-alkylpseudoionone

16. A continuous process for preparing ionones of the general formulae (IV), (V) and (VI) and isomers thereof, which comprises reacting the pseudoionones obtained according to claim 15 to give ionones of the general formulae (IV) to (VI)

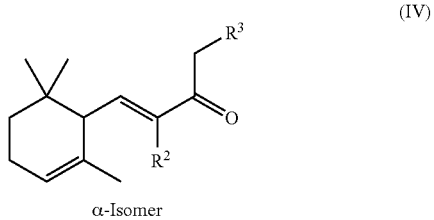

(IV)

α-Isomer

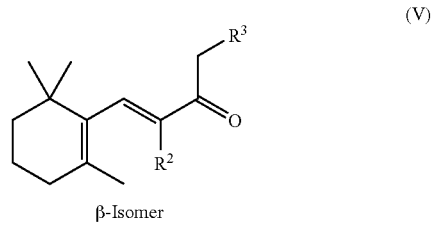

(V)

β-Isomer

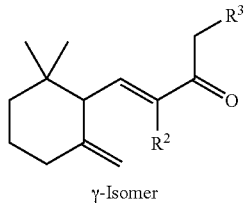

(VI)

γ-Isomer in the form such that the ratio of the n-form ($R^2$=H, $R^3$=alkyl) to the iso-form ($R^2$=alkyl, $R^3$=H) according to claim 15 is maintained.

17. The process according to claim 16, wherein the pseudoionones are reacted with highly concentrated sulfuric acid in the presence of a diluent which is inert under the reaction conditions to give ionones, the reaction temperature being 0–20° C. and the residence time between cyclization and hydrolysis being 120 seconds.

18. A continuous process for preparing jonones of the general fonnulae (IV), (V) and (VI) and isomers thereof, which comprises reacting to pseudoinnones obtained according to claim 1 to give ionones of the general formulae (IV) to (VI)

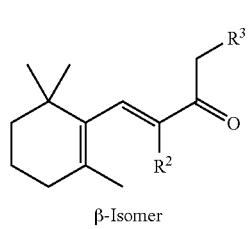

(IV)

α-Isomer

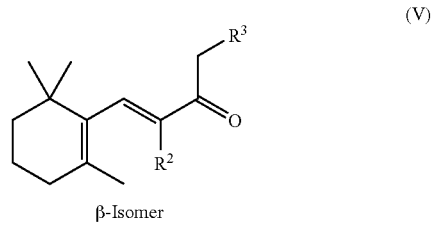

(V)

β-Isomer

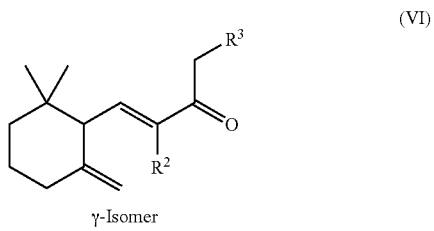

(VI)

γ-Isomer in the form such that the ratio of the n-form ($R^2$=H, $R^3$=alkyl) to the iso-form ($R^2$=alkyl, $R^3$=H) is maintained which contains from 70 to 95% n-alkylpseudoionones and from 5 to 30% isoalkylpseudoionones
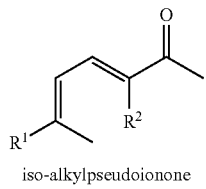
iso-alkylpseudoionone
-continued
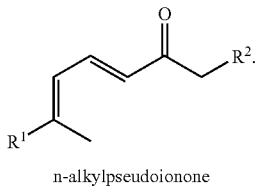
n-alkylpseudoionone
* * * * *

UNITED STATES PATENT AND TRADEMARK OFFICE
CERTIFICATE OF CORRECTION

PATENT NO.         : 7,141,698 B2
APPLICATION NO. : 10/533969
DATED                 : November 28, 2006
INVENTOR(S)      : Walter Dobler et al.

It is certified that error appears in the above-identified patent and that said Letters Patent is hereby corrected as shown below:

In Claim 10, at column 10, line 60, "add in the presence of a dihient which is inert under the" should read -- acid in the presence of a diluent which is inert under the --.

In Claim 12, at column 11, line 2, "concentration of the alkali metal hydroxide used forte reac-" should read -- concentration of the alkali metal hydroxide used for the reac- --.

In Claim 15, at column 11, line 18, "case of reset on with ketones of the general formula (III)" should read -- case of reaction with ketones of the general formula (III) --.

Signed and Sealed this

Seventeenth Day of April, 2007

JON W. DUDAS
*Director of the United States Patent and Trademark Office*